United States Patent
Goble et al.

(10) Patent No.: US 7,488,347 B1
(45) Date of Patent: Feb. 10, 2009

(54) TRANSOSSEOUS GRAFT RETENTION SYSTEM AND METHOD

(75) Inventors: E. Marlowe Goble, Logan, UT (US); T. Wade Fallin, Hyde Park, UT (US); Daniel F. Justin, Logan, UT (US)

(73) Assignee: Medicine Lodge, Inc., Logan, UT (US)

( * ) Notice: Subject to any disclaimer, the term of this patent is extended or adjusted under 35 U.S.C. 154(b) by 499 days.

(21) Appl. No.: 11/030,462

(22) Filed: Jan. 6, 2005

(51) Int. Cl.
*A61F 2/30* (2006.01)
(52) U.S. Cl. .................................................. 623/18.11
(58) Field of Classification Search ................... 606/72, 606/232, 233; 623/13.11–13.18, 14.12, 16.11, 623/17.11, 18.11
See application file for complete search history.

(56) References Cited

U.S. PATENT DOCUMENTS

| | | | |
|---|---|---|---|
| 4,479,271 A * | 10/1984 | Bolesky et al. ........... 623/20.17 |
| 4,502,161 A | 3/1985 | Wall | |
| 4,627,853 A | 12/1986 | Campbell et al. | |
| 4,673,407 A | 6/1987 | Martin | |
| 4,773,910 A | 9/1988 | Chen et al. | |
| 4,927,421 A | 5/1990 | Goble et al. | |
| 4,950,270 A | 8/1990 | Bowman et al. | |
| 5,035,699 A | 7/1991 | Coates | |
| 5,037,439 A | 8/1991 | Albrektsson et al. | |
| 5,067,964 A | 11/1991 | Richmond et al. | |
| 5,092,895 A | 3/1992 | Albrektsson et al. | |
| 5,100,409 A | 3/1992 | Coates et al. | |
| 5,156,616 A * | 10/1992 | Meadows et al. ........... 606/232 |
| 5,176,684 A | 1/1993 | Ferrante et al. | |
| 5,456,721 A | 10/1995 | Legrand | |
| 5,489,311 A | 2/1996 | Cipolletti | |
| 5,569,259 A | 10/1996 | Ferrante et al. | |
| 5,584,835 A | 12/1996 | Greenfield | |
| 5,593,411 A | 1/1997 | Stalcup et al. | |
| 5,601,557 A * | 2/1997 | Hayhurst ................... 606/72 |
| 5,632,745 A | 5/1997 | Schwartz | |
| 5,645,588 A * | 7/1997 | Graf et al. .................. 606/151 |
| 5,674,224 A | 10/1997 | Howell et al. | |
| 5,688,284 A | 11/1997 | Chervitz et al. | |

(Continued)

FOREIGN PATENT DOCUMENTS

WO    WO 89/09578 A1    10/1989

(Continued)

*Primary Examiner*—Eduardo C Robert
*Assistant Examiner*—Michael J Araj
(74) *Attorney, Agent, or Firm*—David W. Meibos; Barbara Daniels; Daniel F. Justin

(57) ABSTRACT

A system for restoring articular cartilage has a cover, an anchor, and a tether that cooperate to retain graft tissue with respect to a graft site. The cover is attached to the anchor via the tether. The tether passes through a tunnel through a bone to which the articular cartilage is attached. The tunnel connects the graft site to an anchoring side of the bone. The anchor is retained proximate the anchoring side such that tension in the tether keeps the cover in place over the tissue graft to capture the tissue graft at the proper position with respect to the graft site. The cover and/or the anchor may be bioabsorbable. The cover may be perforated to permit fluids to access the tissue graft from outside the cover to enhance incorporation of the graft tissue with the graft site. The cover may be formed of rigid or flexible materials.

23 Claims, 6 Drawing Sheets

U.S. PATENT DOCUMENTS

| | | | |
|---|---|---|---|
| 5,743,915 A | 4/1998 | Bertin et al. | |
| 5,766,250 A | 6/1998 | Chervitz et al. | |
| 5,766,255 A | 6/1998 | Slamin et al. | |
| 5,769,899 A | 6/1998 | Schwartz et al. | |
| 5,776,201 A | 7/1998 | Colleran et al. | |
| 5,860,981 A | 1/1999 | Bertin et al. | |
| 5,879,391 A | 3/1999 | Slamin | |
| 5,921,986 A * | 7/1999 | Bonutti | 606/60 |
| 6,066,173 A | 5/2000 | McKernan et al. | |
| 6,068,648 A | 5/2000 | Cole et al. | |
| 6,071,311 A | 6/2000 | O'Neil et al. | |
| 6,099,568 A | 8/2000 | Simonian et al. | |
| 6,120,541 A * | 9/2000 | Johnson | 623/14.12 |
| 6,168,629 B1 | 1/2001 | Timoteo | |
| 6,171,342 B1 | 1/2001 | O'Neil et al. | |
| 6,235,057 B1 | 5/2001 | Roger et al. | |
| 6,283,996 B1 | 9/2001 | Chervitz et al. | |
| 6,371,958 B1 | 4/2002 | Overaker | |
| 6,461,373 B2 | 10/2002 | Wyman et al. | |
| 6,520,964 B2 | 2/2003 | Tallarida et al. | |
| 6,544,267 B1 | 4/2003 | Cole et al. | |
| 6,554,838 B2 | 4/2003 | McGovern et al. | |
| 6,562,071 B2 | 5/2003 | Jarvinen | |
| 6,575,986 B2 | 6/2003 | Overaker | |
| 6,610,067 B2 | 8/2003 | Tallarida et al. | |
| 6,679,917 B2 | 1/2004 | Ek | |
| 6,743,232 B2 | 6/2004 | Overaker et al. | |
| 6,751,143 B2 | 6/2004 | Morgan et al. | |
| 2002/0055783 A1 | 5/2002 | Tallarida et al. | |
| 2002/0120274 A1 | 8/2002 | Overaker et al. | |
| 2002/0120281 A1 | 8/2002 | Overaker | |
| 2002/0138150 A1 | 9/2002 | Leclereq | |
| 2002/0147498 A1 | 10/2002 | Tallarida et al. | |
| 2003/0060887 A1 | 3/2003 | Ek | |
| 2003/0120276 A1 | 6/2003 | Tallarida et al. | |
| 2003/0158606 A1 | 8/2003 | Coon et al. | |
| 2003/0225456 A1 | 12/2003 | Ek | |
| 2003/0225457 A1 | 12/2003 | Justin et al. | |
| 2004/0015170 A1 | 1/2004 | Tallarida et al. | |
| 2004/0148030 A1 | 7/2004 | Ek | |

FOREIGN PATENT DOCUMENTS

| | | |
|---|---|---|
| WO | WO 01/66021 A1 | 9/2001 |
| WO | WO 01/66022 A1 | 9/2001 |
| WO | WO 03/051210 A2 | 6/2003 |
| WO | WO 03/051211 A1 | 6/2003 |

* cited by examiner

TRANSOSSEOUS GRAFT RETENTION SYSTEM AND METHOD

CROSS-REFERENCE TO RELATED APPLICATIONS

The following disclosures are incorporated herein by reference:

U.S. application Ser. No. 10/459,375, filed Jun. 11, 2003, and is entitled LINE LOCK SUTURE ATTACHMENT SYSTEMS AND METHODS;

U.S. application Ser. No. 10/936,376, filed Sep. 7, 2004, and is entitled ADJUSTABLE LINE LOCKS AND METHODS;

U.S. application Ser. No. 10/942,275, filed Sep. 15, 2004, and is entitled LINE LOCK THREADING SYSTEMS AND METHODS;

U.S. application Ser. No. 11/001,866, filed Dec. 1, 2004, and is entitled LINE LOCK SUTURE ATTACHMENT SYSTEMS AND METHODS;

U.S. application Ser. No. 09/970,559, filed Oct. 3, 2001, and is entitled METHOD AND APPARATUS FOR RECONSTRUCTING A LIGAMENT;

U.S. application Ser. No. 10/798,665, filed Mar. 11, 2004, and is entitled IMPLANTS AND RELATED METHODS AND APPARATUS FOR SECURING AN IMPLANT ON AN ARTICULATING SURFACE OF AN ORTHOPEDIC JOINT; and U.S. application Ser. No. 10/901,941, filed Jul. 28, 2004, and is entitled TETHERED JOINT BEARING IMPLANTS AND SYSTEMS.

BACKGROUND OF THE INVENTION

1. The Field of the Invention

The present invention relates generally to restoration of surfaces of articulating joints of the body, and more specifically, to restoration of a surface formed of articular cartilage through the use of a tissue graft.

2. The Relevant Technology

The articulating surfaces of various joints of the body, such as the adjacent surfaces of the tibia and femur, are covered with cartilage that facilitates relative sliding. Due to trauma, disease, or wear, local defects can be formed in such surfaces. Such defects can cause discomfort for a patient and accelerate wear of the remaining cartilage.

Accordingly, several treatments have been developed to address problems with cartilage articulation surfaces. According to one known treatment, a cartilage graft is harvested from some other part of the body (thereby providing an "autograft"), and is positioned at the site of the defect. Via various methods known in the art, graft incorporation may be promoted to help integrate the graft with the surrounding cartilage.

Unfortunately, keeping the cartilage graft in place presents a somewhat unique challenge. According to some known methods, the graft may be fastened to the graft site, or held within a cage attached to the bone behind the articulation surface. Unfortunately, many such retention mechanisms inhibit contact and/or fluid flow between the graft and the surrounding cartilage, thereby inhibiting incorporation. Additionally, some such mechanisms leave components in the body that will not be absorbed by the body, and thus have the potential to become dislodged and damage the articulation surfaces. Further, some such mechanisms are complex and/or difficult to implant in the body, thereby increasing the expense of the operation, the invasiveness of the surgery, the healing time required, and the probability of failure.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to tissue grafts for restoration of cartilage articulation surfaces, including, but not limited to, articulation surfaces of the knee. Those of skill in the art will recognize that the systems and methods described herein may be readily adapted for restoration of other types of tissue, or other types of articulation surfaces.

In this application, a "tunnel" refers to any type of man-made passageway passing partially or completely through a bone. To "capture" a first object with a second object refers to application of pressure on at least one surface of the first object with the second object to keep the first object generally in place. Some relative motion between the two objects may be permitted. Capturing does not require that the second object completely contain or enclose the first object. "Actuation" refers to any type of motion or deformation of an object or of a portion thereof. Thus, a portion of a suture may be "actuated" to form a knot in the suture.

The term "direction," when used in connection with motion of a flexible member such as a line, does not necessarily refer to a static vector. Rather, a "direction" may refer to motion of the line along a pathway, toward one specified end of the pathway. Thus, stating that a line is only able to move along a pathway in one direction means that the line can only be advanced toward one end of the pathway. The line moves along the pathway in one direction even though in the course of advancement along the pathway, segments of the line will simultaneously be moving along a variety of differently-oriented vectors.

A "tether" refers to a member capable of linking two objects to restrict motion of the objects away from each other. A tether need not be a flexible member, but may instead be a rigid link. "Incorporation" of a graft tissue with a graft site does not require that the graft tissue and the graft site become homogeneous; rather, it simply means that linking material is provided in intervening space between the graft tissue and the graft site to bring the exposed surfaces of the graft site and the graft tissue closer to a continuous, smooth shape.

A first object that "substantially encircles" a second object need not extend a full 360° around the second object. Rather, the first object extends more than 180° around the second object. The term "attach" is broadly interpreted to include securement of separate elements to each other, and the integral formation of separate elements with each other. Thus, two portions of an object that are unitarily formed in a single operation may be said to be "attached" together. Furthermore, two objects are attached together if their relationship is such that relative motion between the objects is restricted in at least one direction. Attachment does not require impediment of relative motion in all directions. The term "lock" also does not require restriction of relative motion in all directions.

Figure 1:
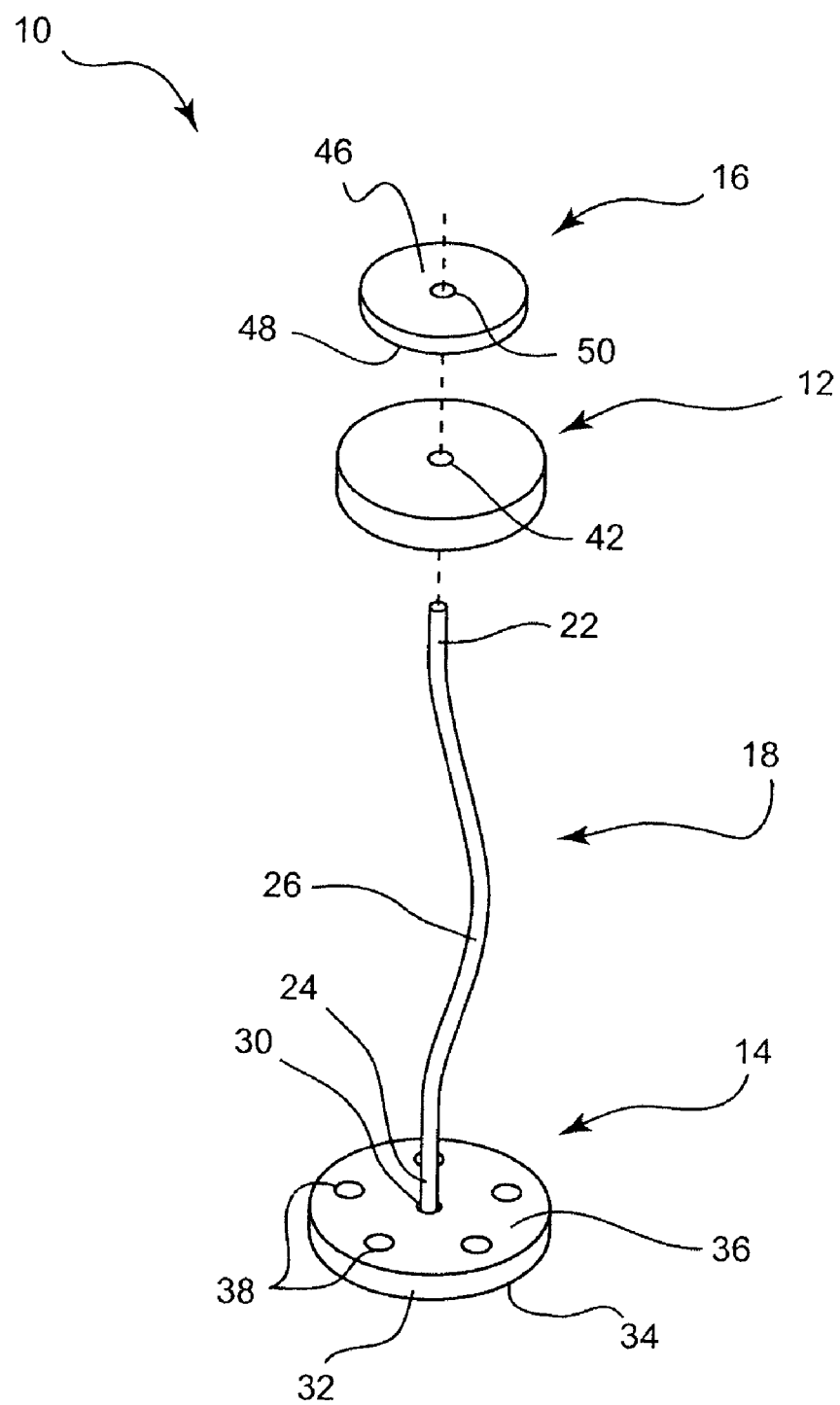
FIG. 1 is an exploded, perspective view of a system for articulation surface repair according to one embodiment of the invention.

Referring to FIG. 1, a perspective view illustrates a graft system according to one embodiment of the invention. As shown, the system 10 has a tissue graft 12 that is designed to be positioned at a graft site (not shown in FIG. 1), which may be a region of articular cartilage in which some of the cartilage is missing due to wear or trauma. The tissue graft 12 may be a piece of cartilage harvested from some other part of the patient's body (an autograft) or from a compatible human donor (an allograft), or from an animal donor (a xenograft). Alternatively, the tissue graft 12 may be artificially formulated (a synthetic graft). The system 10 also has a cover 14, an anchor 16, and a tether in the form of a suture 18. The cover 14, anchor 16, and suture 18 cooperate to keep the tissue graft 12 in place with respect to the graft site.

As shown, the suture 18 has a first end 22 and a second end 24. The second end 24 may initially be attached to the cover 14, and the first end 22 may subsequently be coupled to the anchor 16 in such a manner that the cover 14 is held in place to capture the tissue graft 12 with respect to the graft site, as will be shown and described subsequently in greater detail. The suture 18 also has an intermediate portion 26 between the first end 22 and the second end 24.

The cover 14 has a socket 30 within which the second end 24 of the suture 18 is retained in a substantially permanent manner. The cover 14 also has a periphery 32, an outer surface 34, and a retention surface 36. The outer surface 34 faces outward with respect to the tissue graft 12, and the retention surface 36 faces inward, toward the tissue graft 12. Some part of the retention surface 36 may abut the tissue graft 12 when the system 10 is installed to effectively capture the tissue graft 12.

Optionally, the periphery 32 of the cover 14 may be larger than the tissue graft 12, so that the cover 14 cooperates with the graft site (not shown) to substantially enclose the tissue graft 12. The cover 14 has a generally fluid-permeable structure that permits relatively easy passage of fluids such as synovial fluid and other body fluids, proteins, growth factors, and the like to the tissue graft 12 to simulate regeneration of the articular cartilage or incorporation of the tissue graft 12 into the surrounding articular cartilage. Thus, the cover has a plurality of holes 38 extending from the outer surface 34 to the retention surface 36. In alternative embodiments of the invention, a cover may be sized smaller than a tissue graft to provide retention, but not enclosure, of the tissue graft. A perforated structure may or may not be desirable for such a smaller cover.

The cover 14 may also be bioabsorbable so that, over time, the cover 14 can be absorbed by the body without adversely affecting the operation of joints or other biological systems. The perforated structure of the cover 14 helps to increase the surface area-to-volume ratio of the cover 14, thereby increasing the rate at which the cover 14 is absorbed by the patient's body. The rate of absorption may be tuned to ensure that the necessary incorporation and/or regeneration of the graft site is able to occur before the cover 14 loses its ability to keep the tissue graft 12 in place.

A wide variety of bioabsorbable materials may be used to form the cover 14. Examples of suitable materials include homopolymers and copolymers of lactide, glycolide, trimethylene carbonate, caprolactone, and p-dioxanone and blends or other combinations thereof and equivalents thereof. Examples of non-absorbable homopolymers and copolymers materials include non-absorbable polyesters, polyorthoesters, polyanhydrides, polycarbonates, polyurethanes, polyamides and polyalkylene oxides, polyolefins, and polyacetals and equivalents thereof. Bioactive and absorbable glasses or ceramics comprising calcium phosphates and other biocompatible metal oxides (i.e., CaO) may also be used.

The tissue graft 12 may have a disc-like shape, as shown, or any other shape. Different shapes and sizes may be selected to suit a variety of graft site shapes. The tissue graft 12 has a central opening 42 through which the suture 18 is able to pass.

The shape of the cover 14 may be matched to that of the tissue graft 12. Thus, in the system 10 of FIG. 1, the cover 14 has a disc-like shape that corresponds to the disc-like shape of the tissue graft 12. The cover 14 may also be contoured in three dimensions to define a substantially continuous contour in combination with the surrounding natural cartilage. Thus, the edges of the cover 14 do not protrude with respect to the surrounding cartilage when the cover 14 is installed. Accordingly, the cover 14 does not significantly abrade the articular surface that articulates against the cover 14.

The anchor 16 may also have a disc-like shape. The anchor 16 is designed to retain the first end 22 of the suture 18 via knotting or other methods, as will be discussed subsequently. The anchor 16 may have an outer surface 46 that faces generally outward with respect to the tissue graft 12, and the retention surface 48 faces generally inward, toward the tissue graft 12. The anchor 16 also has a central opening 50 that extends from the outer surface 46 to the retention surface 48. The central opening 50 is sized to permit passage of the suture 18 therethrough to facilitate retention of the first end 22.

Optionally, the anchor 16 may also be bioabsorbable. The rate of absorption of the anchor 16 may be tuned to ensure that the necessary incorporation and/or regeneration of the graft site is able to occur before the anchor 16 loses its ability to keep the first end 22 in place.

The cover 14, anchor 16, and suture 18 are relatively easily installed using procedures that are less invasive than many known graft placement procedures. Furthermore, the tissue graft 12 can be securely retained in a manner that does not inhibit tissue incorporation or regeneration. The manner in which the system 10 is installed will be set forth in greater detail in the following description of FIGS. 2 through 5.

Figure 2:
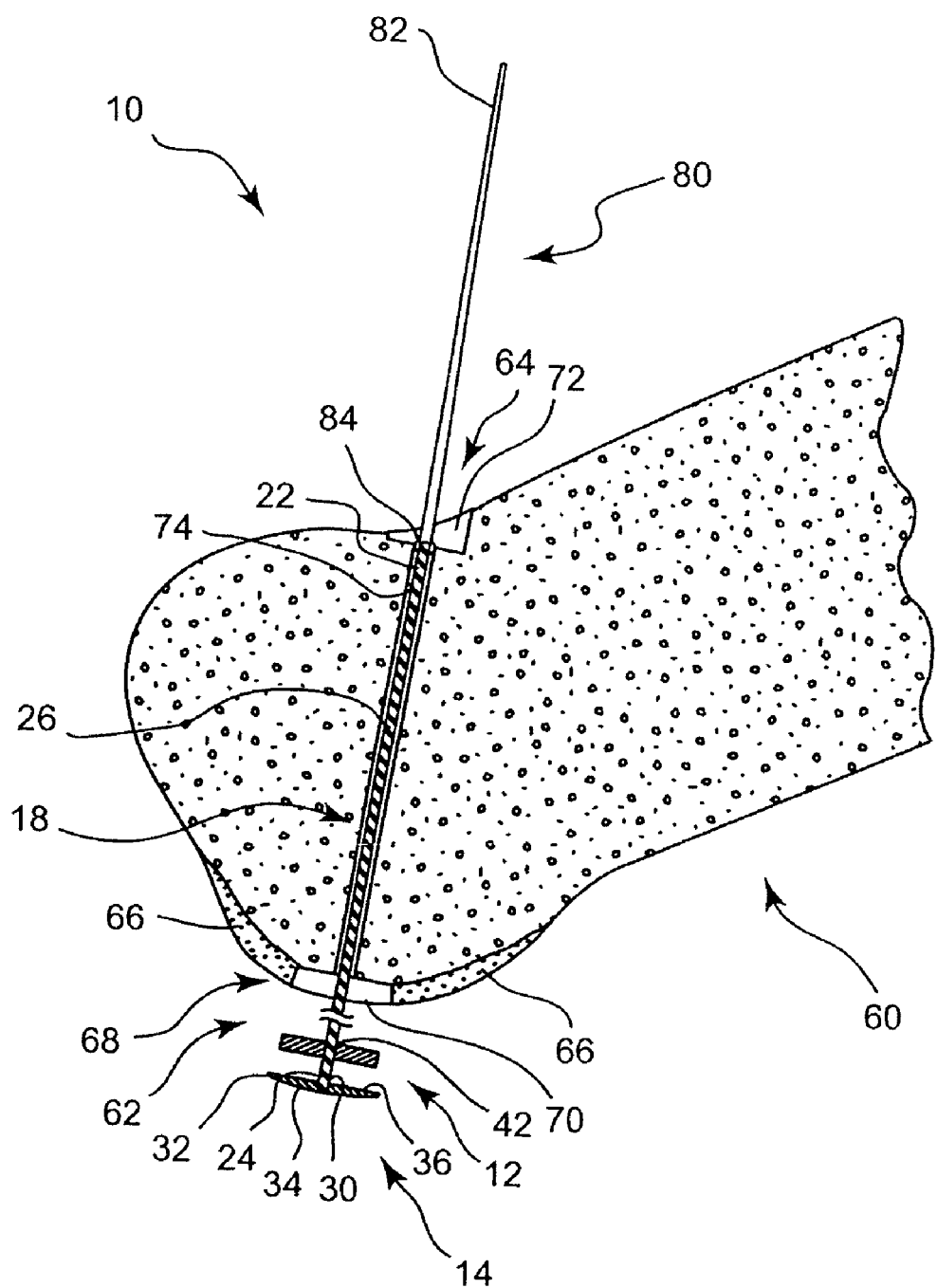
FIG. 2 is a side elevation, section view of a femur with a tunnel formed therein, in which the suture is inserted through the tissue graft and partially through the tunnel.

Referring to FIG. 2, a side elevation, section view illustrates an initial step in the installation of the system 10 in a patient, or more specifically, in a part of a joint such as the knee. More precisely, FIG. 2 illustrates the end of a bone 60, which may be a patient's femur. The bone 60 has a graft side 62 to which the tissue graft 12 is to be applied, and an anchoring side 64 to which the anchor 16 is to be coupled. The graft side 62 has articular cartilage 66 that forms a smooth surface along which a corresponding articular surface of the tibia is easily slidable.

The graft side 62 also has a graft site 68, which is the defect in the articular cartilage 66 that is to be repaired through the use of the tissue graft 12. Thus, the graft site 68 may have a cavity 70, which may have a shape defined by the particular wear or trauma that necessitated the use of the graft operation.

Alternatively, reaming or other operations may be performed at the graft site 68 to remove degenerative tissue and/or provide the cavity 70 with a shape conducive to rapid incorporation and/or regeneration of the tissue graft 12. For example, prior to installation of the tissue graft 12, the cavity 70 may be shaped to match the shape of the cavity 70 to the tissue graft 12.

As shown, the anchoring side 64 also has a cavity 72, which may be reamed or otherwise formed in a manner that facilitates retention of the anchor 16 therein, as will be described subsequently. A tunnel 74 is formed, for example, via drilling, to provide communication between the graft side 62 and the anchoring side 64. The tunnel 74 may have a generally circular cross sectional shape, and may extend from the cavity 70 of the graft site 68 to the cavity 72 of the anchoring side 64.

Initially, the graft site 62 may be exposed by cutting open the skin and spreading any muscle tissue and tendons that cover the graft site 68. The cavity 70 may then be shaped as desired. The anchoring side 64 need not necessarily be exposed at this stage, but may optionally be exposed to facilitate shaping of the cavity 72.

Once the graft site 62 has been prepared, the first end 22 of the suture 18 may be inserted through the central opening 42 of the tissue graft 12. The first end 22 may then be advanced through the tunnel 74 through the use of a needle 80. As shown, the needle 80 has a tip 82 with a sharpened shape, and an eyelet 84. The first end 22 may be secured to the needle 80 by inserting it through the eyelet 84 and, for example, tying it with a conventional knot.

Once the first end 22 has been secured to the needle 80, the tip 82 of the needle 80 may be inserted through the cavity 70 of the graft side 62 and into the tunnel 74. The needle 80 may be pushed through the tunnel 74 until the tip 82 exits the tunnel 74 on the anchoring side 64 of the bone 60. The needle 80 may be further actuated to draw the first end 22 through the tunnel 74 and out of the tunnel 74 at the anchoring side 64. If the anchoring side 64 has not yet been exposed, this may entail pushing the tip 82 through the skin covering the anchoring side 64. If desired, the needle 80 may be longer than is illustrated in FIG. 2 to ensure that a portion of the needle 80 is always exposed and easily actuated during performance of the above-described process.

Figure 3:
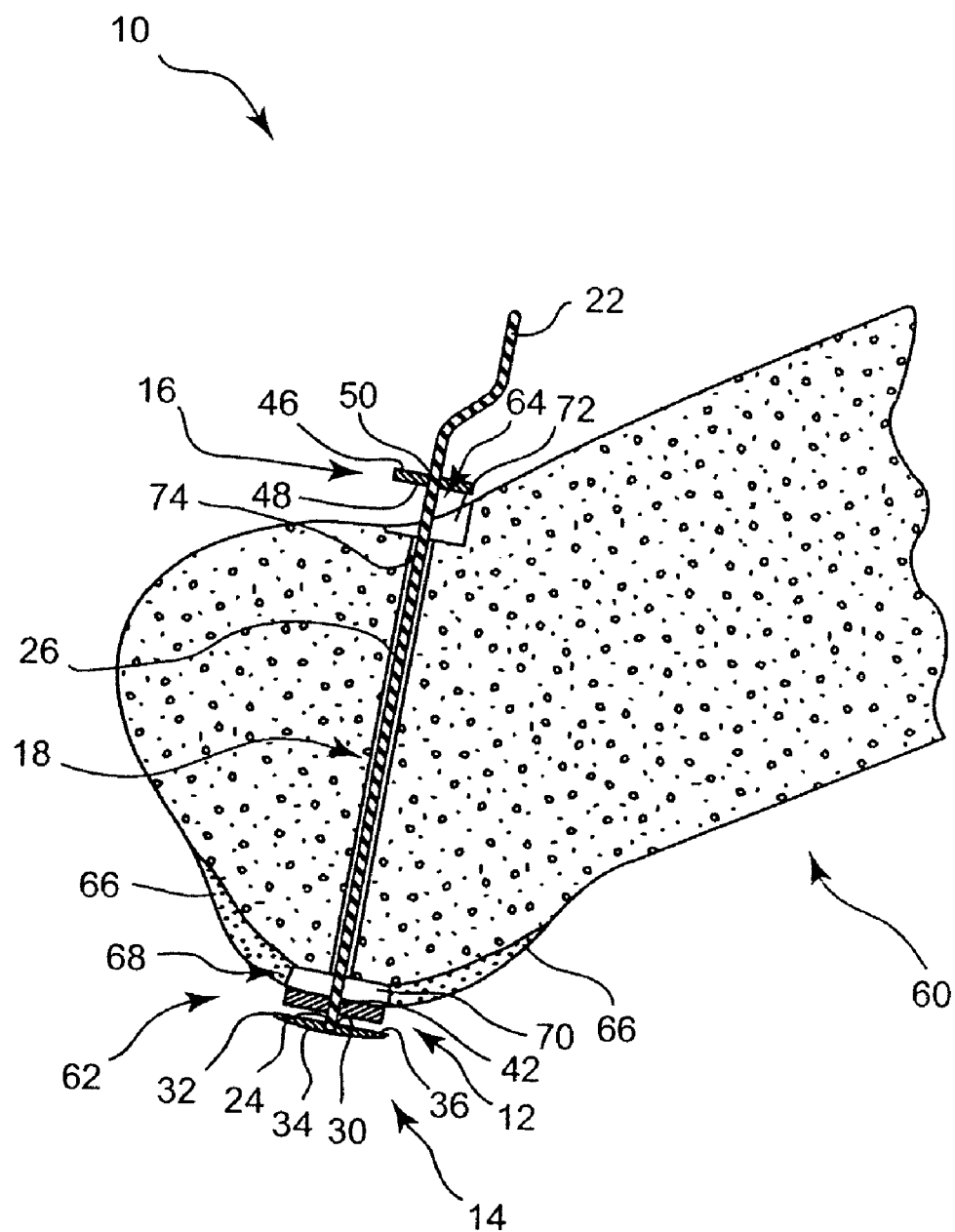
FIG. 3 is a side elevation, section view of the femur, in which the suture is fully drawn through the tunnel and through the corresponding anchor.

Referring to FIG. 3, a side elevation, section view illustrates another step in the installation of the system 10 in the patient. As shown, the first end 22 has passed fully through the tunnel 74 to position the second end 24, the cover 14, and the tissue graft 12 proximate the graft site 68. The needle 80 has been removed from the first end 22, for example, by untying or cutting away the knot by which the first end 22 was attached to the eyelet 84.

Furthermore, the first end 22 has also been inserted through the anchor 16. More precisely, the first end 22 has been inserted through the central opening 50 of the anchor 16 to pass from the retention surface 48 to the outer surface 46. The anchor 16 has been further actuated along the suture 18 until it rests within the cavity 72 of the anchoring side 64. The anchor 16 is sized to fit into the cavity 72, but not into the tunnel 74. Thus, the cavity 72 defines a shoulder on which the anchor 16 is able to rest due to abutment of the retention surface 48 against the shoulder.

Figure 4:
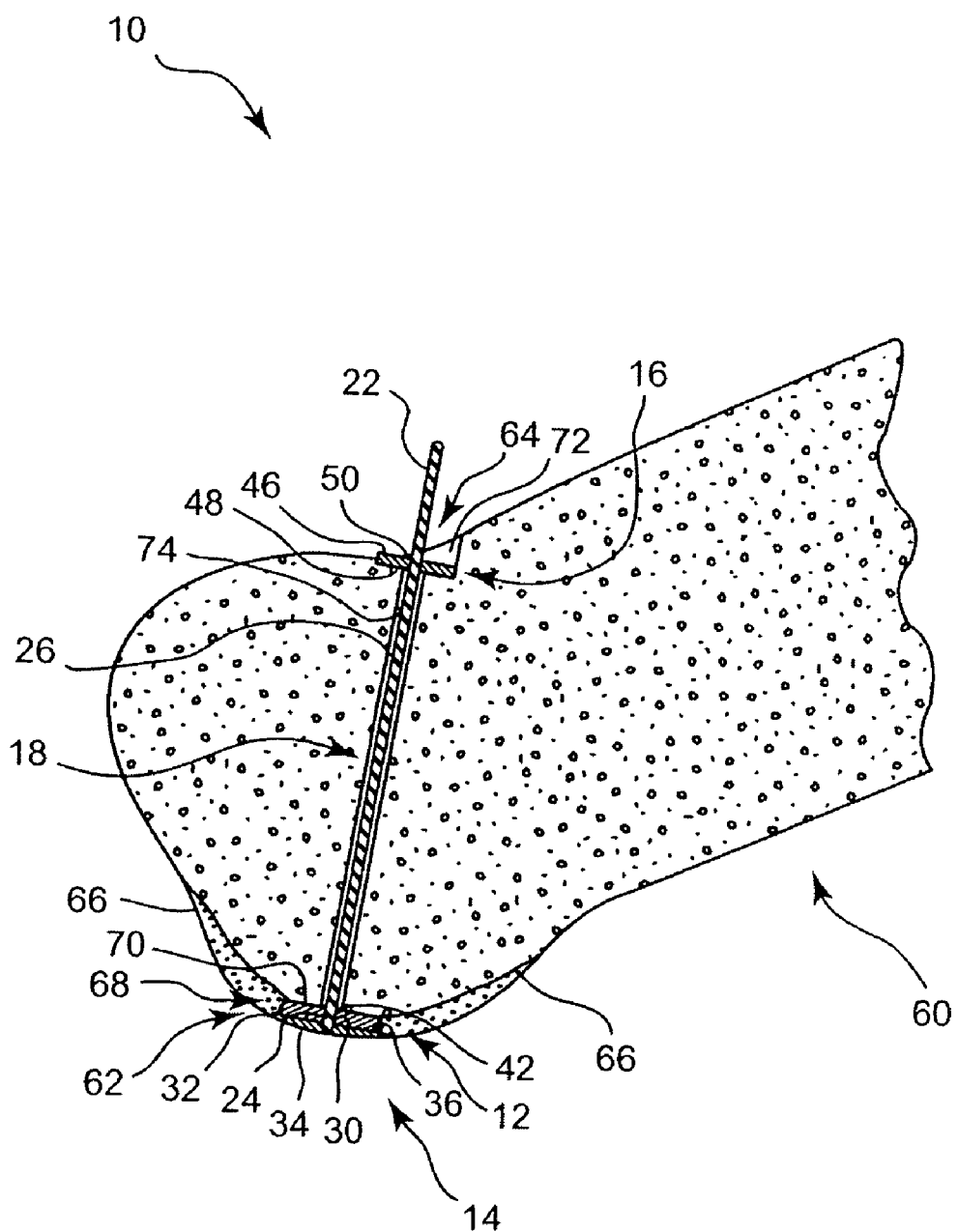
FIG. 4 is a side elevation, section view of the femur, in which the suture is tightened to urge the tissue graft toward the graft site via the cover.

Referring to FIG. 4, a side elevation, section view illustrates another step in the installation of the system 10 in the patient. The suture 18 has been further drawn through the central opening 50 of the anchor 16 to draw the cover 14 against the articular cartilage 66, thereby positioning the tissue graft 12 within the cavity 70 of the graft site 68. The intermediate portion 26 of the suture 18 has been drawn taught within the tunnel 74 so that tension in the intermediate portion 26 holds the cover 14 in place against the articulate cartilage 66, and holds the anchor 16 in place against the shoulder defined by the cavity of the anchoring side 64.

The retention surface 36 of the cover 14 may press directly against the tissue graft 12 to keep it in place by pressing it against the graft site 68. Alternatively, the portion of the retention surface 36 adjacent to the periphery 32 of the cover 14 may rest on the articular cartilage 66 surrounding the graft site 66 to form a space within which the tissue graft 12 has some freedom of movement. Such freedom of movement may enhance fluid access to the tissue graft 12. The tissue graft 12 is still "secured" to the graft site 68 because it is unable to leave the space defined by cooperation of the cover 14 with the graft site 68.

Figure 5:
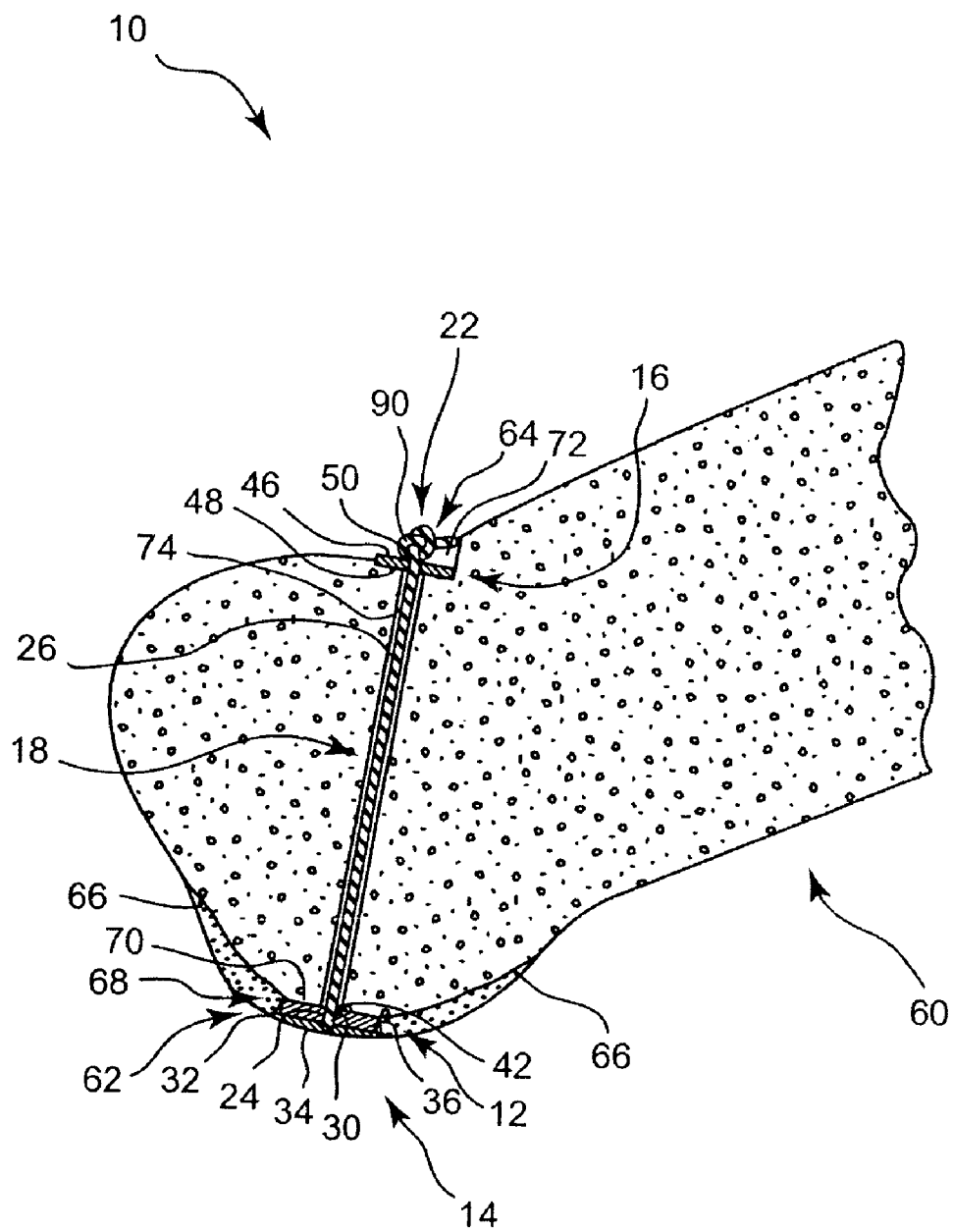
FIG. 5 is a side elevation, section view of the femur, in which a portion of the suture is locked with respect to the anchor to maintain tension in the suture.

Referring to FIG. 5, a side elevation, section view illustrates yet another step in the installation of the system 10 in the patient. As shown, the suture 18 has been kept taught while a knot 90 has been tied in the first end 22, adjacent to the anchor 16. The knot 90 is too large to pass through the central opening 50 of the anchor 16, and therefore preserves the tension in the intermediate portion 26 of the suture 18. Thus, the cover 14 and the anchor 16 remain in place to keep the tissue graft 12 properly positioned within the graft site 68 while incorporation and/or regeneration take place.

The knot 90 therefore serves as a retention feature that keeps the first end 22 in place proximate the anchoring side 64 of the bone 60, independently of positioning the first end 22 proximate the anchoring side. Thus, unlike a bone screw, the suture 18 is retained in the bone 60 by actuating the first end 22 to form a retention feature, i.e., the knot 90, after positioning of the first end 22 proximate the anchoring side. In the embodiment of FIGS. 1-5, the knot 90 operates in conjunction with the anchor 16 to retain the first end 22. In alternative embodiments, the anchor 16 may be omitted in favor of abutment of the knot 90 directly against the anchoring side 64.

The tissues proximate the graft site 68 and/or the anchoring side 64 of the bone 60 may then be closed, and the healing process may commence. After sufficient incorporation and/or regeneration has occurred, the tissue graft 12 remains in place without the aid of the remainder of the system 10. Accordingly, the cover 14 and/or the anchor 16 may then be absorbed by the body without adversely affecting the healing of the graft site 68.

The principles of the present invention may be applied to a wide variety of embodiments besides that of FIGS. 1-5. For example, in place of the suture 18, an alternative flexible tether (not shown) such as a cable, elastic band, or the like may be used. A flexible barbed line could be ratcheted into a tubular anchor design to receive the barbs. Furthermore, if suture is used, the suture could be braided or monofilament, coated or uncoated, and absorbable or non-absorbable. Such a suture may be formed of natural or synthetic materials, and may be formed of a polymer, a metal, or some combination thereof. An elastomer may even be used. Examples of sutures that may be suitable for the present invention include, but are not limited to VICRYL, coated VICRYL, PDS, catgut, chromic catgut, PROLINE, nylon, ETHIBOND, braided fiberwire, silk, and steel.

Alternatively, a "tether" need not be a flexible line, but may instead be rigid. For example, a cover and an anchor may be tethered together via a rigid rod (not shown) or the like. A rigid rod may have a threaded end that enables the rod to be tensioned and secured with respect to the anchor.

An anchor according to the invention need not be a disc, but may instead have any shape capable of engaging the bone to keep the anchor in place. According to one example, an anchor (not shown) may have an expandable periphery designed to extend outward to engage the wall of the tunnel 74, rather than resting on the shoulder defined by the cavity 72 of the anchoring side 64. An anchor according to the invention therefore need not require that the tunnel 74 extend completely through the bone 60; rather, with some anchor embodiments, a blind hole (not shown) may suffice. An anchor may alternatively have a threaded exterior designed to engage the bone tunnel.

Furthermore, an anchor according to the invention may employ a wide variety of tether retention mechanisms. For example, an anchor may retain a suture by inserting two separate lengths of suture through separate holes of the anchor and then knotting them together, as will be shown and described in connection with FIG. 6. An anchor may alternatively be crimped around a suture to retain the suture, or may have a collet or other gripping device.

As another alternative, an anchor according to the invention may be designed to permit relative motion between the anchor and the suture along only one direction. For example, the anchor may have holes arranged in such a pattern that one or two suture lengths can be inserted therethrough along a pattern that permits motion of the suture along the pattern in only one direction. Alternatively, an anchor (not shown) may have a ball within a conical cavity through which the suture passes; the ball is drawn to impinge against the suture in response to motion of the suture toward the narrow portion of the cavity, but permits relatively free motion of the suture toward the broad portion of the cavity. The foregoing are merely examples; any known one-way locking device may be used within the scope of the present invention to facilitate tensioning and/or retention of a tether by an anchor.

In yet other alternative embodiments, different cover arrangements may be used. According to one alternative embodiment, a flexible cover may be used in place of the cover 14 of FIGS. 1-5. Such an arrangement will be shown and described in connection with FIG. 6.

Figure 6:
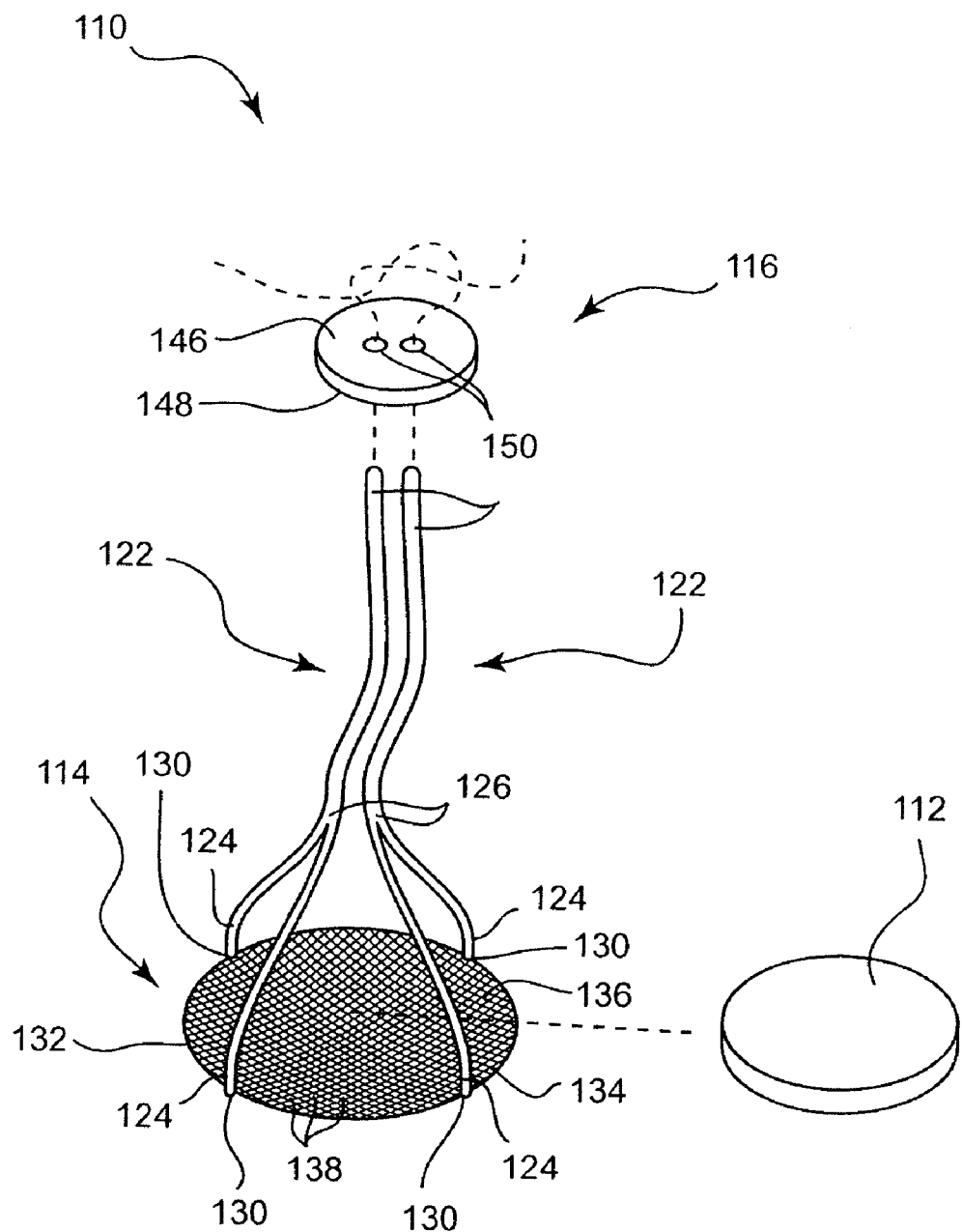
FIG. 6 is an exploded, perspective view of a system for articulation surface repair according to one alternative embodiment of the invention.

Referring to FIG. 6, a perspective view illustrates a graft system 110 according to one alternative embodiment of the invention. As shown, the graft system 110 is designed to (retain a tissue graft 112 with respect to a graft site such as the graft site 68 of FIGS. 2 through 5. The graft system 110 has a cover 114, an anchor 116, a first suture 118, and a second suture 120.

Each of the first and second sutures 118, 120 has a first end 122 and two second ends 124, each of which is attached to the cover 114. Further, each of the first and second sutures 118, 120 has an intermediate portion in which a junction 126 is present. At the junction 126 of each of the sutures 118 and 120, two separate strands converge from the second ends 124 to provide a single strand that extends to the first end 122.

The cover 114 is formed of a flexible mesh such as a fabric. As in the previous embodiment, the cover 114 has a disc-like shape that corresponds to and is slightly broader than that of the tissue graft 112. The cover 114 has four attachment points 130 at which the second ends 124 of the sutures 118, 120 are attached to the cover 114. The attachment points 130 are distributed relatively uniformly about a periphery 132 of the cover 114 so that the periphery 132 is relatively uniformly drawn by tension on the first and second sutures 118, 120.

As in the previous embodiment, the cover 114 has an outer surface 134 that faces outward with respect to the tissue graft 112, and a retention surface 136 that faces the tissue graft 112 and keeps it in place. The mesh structure of the cover 114 provides an array of voids 138 that serve as passageways through the cover 114 to permit fluids such as synovial fluid and other body fluids, proteins, growth factors, and the like to reach the tissue graft 112 from outside the cover 114. The cover 114 may be bioabsorbable, and may be designed to resist absorption long enough for the graft tissue 112 to become sufficiently incorporated into the articular cartilage 66 to remain in place independently.

Many different materials may be used to form the cover 114. Some biocompatible materials that may be used to form the cover 114 include, but are not limited to, Polyester cloth (Dacron), Polyester sheeting (Mylar), Polyester Felt, Polyester Knit, woven Polyester, Polyester Knitted Velour, PTFE Felt, PTFE Knit, acrylic cloth (Orlon), polyvinyl sponge (Ivalon), polyvinyl cloth (Vinyon-N), polyethylene (PE) mesh, polypropylene (PP, Marlex, Prolene) mesh, polytetrafluoroethylene (PTFE, teflon) mesh, expanded polytetrafluoroethylene (ePTFE, gore-tex) mesh, polyvinylidene fluoride (PVDF) mesh, ethyl vinyl acetate (EVA) mesh, nylon/polyamide mesh, thermoplastic polyurethane (TPU) mesh, polyetheretherketone (PEEK) mesh, composite polymer mesh, tantalum mesh, Nickel-Titanium (nitinol, NiTi) mesh, Titanium (Ti) mesh, stainless steel (SS) mesh, composite metal mesh, and silicone mesh. The foregoing materials are biocompatible, but may not necessarily be bioabsorbable.

Some specific examples of such materials include Cook SURGISIS Soft Tissue Graft, Gore DUALMESH Biomaterial, Gore SEAMGUARD Staple Line Reinforcement Material, Gore MYCROMESH, GORE-TEX ACUSEAL Cardiovascular Patch, Gore PRECLUDE Pericardial Membrane, Gore Subcutaneous Augmentation Material, Gore PRECLUDE MVP Dura Substitute, Gore Collagen Coated Knitted Polyester Graft, GORE-TEX Regenerative Membrane, GORE-TEX Titanium Reinforced Regenerative Membrane, Bard OEM Textiles, Bard COMPOSIX Mesh, Bard VISILEX Mesh, Genzyme Biosurgery SEPRAMESH, POREX Meshes, Textile Development Associates SPUNBOND Fabrics, Boston Scientific OEM Textiles, Boston Scientific HEMASHIELD PLATINUM FINESSE Patch, Boston Scientific TRELEX Natural Mesh, Boston Scientific ADVANTAGE Mesh, Atrium Medical PROLITE Mesh, Tricomed S. A. DALLOP Mesh, Tricomed S. A. DALLOP PP Mesh, Ethicon PROLENE Mesh, Ethicon PROCEED Surgical Mesh, Ethicon ULTRAPRO Mesh, and Ethicon MERSILENE Mesh. Those of skill in the art will recognize that other materials may be used.

Further, a wide variety of materials are both biocompatible and bioabsorbable, and may thus be advantageously used to form the cover 114. Some bioabsorbable materials that may be used to form the cover 114 include, but are not limited to, polyglycolic acid (PGA, Dexon), polyglactin (Vicryl) mesh, collagen matrix mesh (human, bovine, or porcine), carbon fiber mesh, Polylactic acid (PLA) mesh, poly 1-lactic acid (PLLA) mesh, Trimethylene Carbonate (TMC) mesh, polydiaxanone (PDS) mesh, oxidized regenerated cellulose (ORC) fabric, poly DL-lactic-co-glycolic acid (PLGA), tricalcium phosphate (TCP), and hydroxy-apatite (HA).

Some specific examples of such materials include Gore SEAMGUARD Bioabsorbable Staple Line Reinforcement Material, Gore RESOLUT XT Regenerative Bioabsorbable Membrane, Gore RESOLUT ADAPT Regenerative Bioabsorbable Membrane, Gore OSSEOQUEST Regenerative Membrane, Textile Development Associates Absorbable Textiles, Genzyme Biosurgery SEPRAFILM, and Ethicon VICRYL Mesh. Those of skill in the art will recognize that other materials may be used.

The anchor 116 of the system 110 of FIG. 6 is also configured differently from that of the system 10 described previously. The anchor 116 has a disc-like shape with an outer surface 146 that faces outward with respect to the tissue graft 112, and a retention surface 148 that faces the tissue graft 112 and abuts a bony surface such as the shoulder defined by the cavity 72 of FIGS. 2 through 5. Additionally, the anchor 116 has two central openings 150 that extend from the retention surface 148 to the outer surface 146. The first ends 122 of the first and second sutures 118, 120 are able to pass through the central openings 150.

Then, the first ends 122 may be tied together via a simple overhand knot, as indicated by the dashed lines in FIG. 6. Alternatively, any other knot may be used. The knot then serves as a retention feature that keeps the first end 122 in place proximate an anchoring side of a bone, in a manner similar to that of the knot 90 of the previous embodiment. Usage of the first and second sutures 118, 120 in a parallel arrangement contributes to the torsional stability of the system 110.

The system 110 of FIG. 6 may be installed in a patient in a manner similar to that of the system 10. Accordingly, the method described in connection with FIGS. 2 through 5 is largely applicable to the system 110. More particularly, with reference to the bone 60 of FIGS. 2 through 5, the graft site 68 may first be exposed, and then the tunnel 74, and optionally the cavities 70, 72, may be formed. The graft tissue 112 may be positioned to rest on the retention surface 136 of the cover 114. The graft tissue 112 has no central opening, and is instead kept in place via the flexibility of the retention surface 136 and the sutures 118, 120 that partially enclose it.

The sutures 118, 120 may then be attached to a needle, such as the needle 80, and inserted through the tunnel 74. According to one example, one of the first ends 122 of the sutures 118, 120 may be inserted through the eyelet 84 of the needle 80, and the first ends 122 may then be tied together to attach both of the sutures 118, 120 to the needle 80. The needle 80 may be inserted through the tunnel 74 to draw the first ends 122 through the tunnel 74.

The first ends 122 may then be inserted through the central openings 150 of the anchor 116 and the sutures 118, 120 may be tensioned to draw the tissue graft 112 into the cavity 70 of the graft site 68 via the cover 114. The periphery 132 of the cover 114 may then rest against the articular cartilage 66 surrounding the graft site 68 to form a compartment within which the tissue graft 112 is securely retained. Once the first and second sutures 118, 120 have been properly tensioned, the first ends 122 of the sutures 118, 120 may be tied together in the manner shown by the dashed lines to maintain the tension in the sutures 118, 120 thereby keeping the tissue graft 112 in place.

The tissues proximate the graft site 68 and/or the anchoring side 64 of the bone 60 may then be closed, and the healing process may commence. As in the previous embodiment, incorporation and/or regeneration occurs, and the tissue graft 112 remains in place without the aid of the remainder of the system 110. Accordingly, the cover 114 and/or the anchor 116 may then be absorbed by the body without adversely affecting the healing of the graft site 68.

The present invention has particular relevance to surgery, and more particularly to articulation surface restoration. However, the principles, structures, and methods of the present invention may also be extended to other fields, including restoration of other types of tissue, or other types of articulation surfaces.

The present invention may be embodied in other specific forms without departing from its spirit or essential characteristics. For example, above are described various alternative examples of articulation surface restoration systems. It is appreciated that various features of the above-described examples can be mixed and matched to form a variety of other alternatives, each of which may have a different threading system according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for promoting healing of a cartilage graft site, the system comprising:
    a cartilage graft;
    a tether having a first portion and a second portion, the tether having a length sufficient to pass through a tunnel formed in a bone to extend from an anchoring side of the bone to a cartilage graft site on an articular surface of the bone; and
    a cover attachable to the second portion, wherein the cover is shaped to capture the cartilage graft in response to tension on the tether to promote healing of the cartilage graft site via incorporation of the cartilage graft with the cartilage graft site;
    wherein the first portion of the tether comprises a retention feature that is actuatable independently of positioning the first portion proximate an anchoring side of the bone to attach the first portion to the anchoring side;
    wherein the cover is shaped to hold the cartilage graft against the cartilage graft site without significantly interfering with articulation of the articular surface.

2. The system of claim 1, wherein the cover is formed substantially of a bioabsorbable material.

3. The system of claim 1, wherein the cover has a permeable structure selected to permit fluid to reach the cartilage graft from outside the cover to promote incorporation of the cartilage graft with the cartilage graft site.

4. The system of claim 1, further comprising an anchor attachable to the first portion, wherein the anchor is shaped to abut the bone to maintain tension in the tether.

5. The system of claim 4, wherein the anchor is configured to permit relative motion between the anchor and the tether only along a direction that corresponds to increasing tension in the tether.

6. The system of claim 1, wherein the cartilage graft comprises a passageway through which the tether is insertable such that the cartilage graft substantially encircles a length of the tether.

7. The system of claim 1, wherein the cover comprises a flexible mesh having a periphery, wherein the periphery comprises a plurality of attachment points coupled to the tether such that multiple portions of the tether extend around a periphery of the cartilage graft.

8. The system of claim 1, wherein the cover is attached to the second portion.

9. The system of claim 1, wherein the tether comprises a flexible member.

10. A system for promoting healing of a cartilage graft site within surrounding natural cartilage, the system comprising:
    a cartilage graft;
    a cover positionable at a cartilage graft on an articular surface of a bone site to promote healing of the cartilage graft site via incorporation of the cartilage graft with the cartilage graft site while defining a substantially continuous contour in combination with the surrounding natural cartilage;
    a tether having a first portion and a second portion, wherein the second portion is configured to be coupled to the cover; and an anchor attachable to the first portion, wherein the anchor is shaped to abut the bone proximate an anchoring side of the bone to maintain tension in the tether;

wherein the tether has a length sufficient to pass through a tunnel formed in the bone to position the second portion proximate the cartilage graft site.

11. The system of claim 10, further comprising a cover attachable to the second portion, wherein the cover is shaped to capture the cartilage graft in response to tension on the tether.

12. The system of claim 11, wherein the cover is formed substantially of a bioabsorbable material.

13. The system of claim 11, wherein the cover has a permeable structure selected to permit fluid to reach the cartilage graft from outside the cover to promote incorporation of the cartilage graft with the cartilage graft site.

14. The system of claim 11, wherein the cover comprises a flexible mesh having a periphery, wherein the periphery comprises a plurality of attachment points coupled to the tether such that multiple portions of the tether extend around a periphery of the cartilage graft.

15. The system of claim 10, wherein the anchor is configured to permit relative motion between the anchor and the tether only along a direction that corresponds to increasing tension in the tether.

16. The system of claim 10, wherein the cartilage graft comprises a passageway through which the tether is insertable such that the cartilage graft substantially encircles a length of the tether.

17. The system of claim 10, wherein the tether comprises a flexible member.

18. A method for retaining a cartilage graft, the method comprising:

positioning the cartilage graft between a cartilage graft site on an articular surface of a bone and a cover attached to a second portion of a tether;

exerting tension on the tether;

urging the cover toward the cartilage graft site in response to exertion of the tension, thereby capturing the cartilage graft to promote healing of the cartilage graft site via incorporation of the cartilage graft with the cartilage graft site;

positioning a first portion of the tether proximate the bone; and attaching the first portion to the bone independently of positioning the first portion proximate the bone.

19. The method of claim 18, wherein the cover is formed substantially of a bioabsorbable material.

20. The method of claim 18, wherein attaching the first portion to the bone comprises:

attaching the first portion to an anchor; and positioning the anchor to abut the bone to maintain tension in the tether.

21. The method of claim 20, wherein the tether comprises a flexible member, wherein exerting tension on the tether comprises:

advancing the tether with respect to the anchor along a direction that corresponds to increasing tension in the tether; and locking a position of the tether with respect to the anchor to substantially prevent relative motion between the anchor and tether to release the tension.

22. The method of claim 18, further comprising inserting the tether through a passageway of the cartilage graft such that the cartilage graft substantially encircles a length of the tether.

23. The method of claim 18, wherein the cover comprises a flexible mesh having a periphery, wherein the periphery comprises a plurality of attachment points coupled to the tether, wherein positioning the cartilage graft between the cartilage graft site and the cover comprises positioning the cartilage graft such that multiple portions of the tether extend around a periphery of the cartilage graft.

* * * * *

UNITED STATES PATENT AND TRADEMARK OFFICE
CERTIFICATE OF CORRECTION

| | |
|---|---|
| PATENT NO. | : 7,488,347 B1 |
| APPLICATION NO. | : 11/030462 |
| DATED | : February 10, 2009 |
| INVENTOR(S) | : E. Marlowe Goble, T. Wade Fallin and Daniel F. Justin |

Page 1 of 1

It is certified that error appears in the above-identified patent and that said Letters Patent is hereby corrected as shown below:

Column 1, Line 9 ADD -"which carries Applicants' Docket No. 13447.35",- after "2003,".

Column 1, Line 12 ADD -"which carries Applicants' Docket No. MLI-15",- after "2004,".

Column 1, Line 15 ADD -"which carries Applicants' Docket No. MLI-16",- after "2004,".

Column 1, Line 18 ADD -"which carries Applicants' Docket No. MLI-17",- after "2004,".

Column 1, Line 21 ADD -"which carries Applicants' Docket No. GOBLE-1",- after "2001,".

Column 1, Line 24 ADD -"which carries Applicants' Docket No. 13447.43",- after "2004,".

Column 1, Line 31 ADD -"which carries Applicants' Docket No. 13447.45.1",- after "2004,".

Column 7, Line 41, that portion reading "(retain" should read –retain-.

Signed and Sealed this

Fourth Day of August, 2009

JOHN DOLL
*Acting Director of the United States Patent and Trademark Office*